US008211291B2

(12) United States Patent
Flechsig et al.

(10) Patent No.: US 8,211,291 B2
(45) Date of Patent: Jul. 3, 2012

(54) SENSOR APPARATUS FOR AN ELECTROCHEMICAL MEASURING DEVICE AND METHOD FOR CARRYING OUT ELECTROCHEMICAL MEASUREMENTS

(75) Inventors: Gerd-Uwe Flechsig, Teterow (DE); Jan Gimsa, Rostock (DE); Peter Gründler, Dresden (DE); Harald Grabow, Sildemow (DE)

(73) Assignee: Universitaet Rostock, Rostock (DE)

( * ) Notice: Subject to any disclaimer, the term of this patent is extended or adjusted under 35 U.S.C. 154(b) by 855 days.

(21) Appl. No.: 12/278,672

(22) PCT Filed: Feb. 6, 2007

(86) PCT No.: PCT/EP2007/001132
§ 371 (c)(1),
(2), (4) Date: Nov. 7, 2008

(87) PCT Pub. No.: WO2007/090674
PCT Pub. Date: Aug. 16, 2007

(65) Prior Publication Data
US 2009/0184001 A1    Jul. 23, 2009

(30) Foreign Application Priority Data
Feb. 7, 2006   (DE) .................. 10 2006 006 347

(51) Int. Cl.
  G01F 1/64    (2006.01)
  G01N 17/00   (2006.01)
  G01N 27/26   (2006.01)
(52) U.S. Cl. ... 205/775; 204/400; 204/406; 219/121.48; 373/33
(58) Field of Classification Search .................. 204/406, 204/547, 400; 324/666, 673, 678, 691, 700; 205/775; 219/121.48, 121.52, 121.53; 373/33–36, 373/70, 79–84
See application file for complete search history.

(56) References Cited

U.S. PATENT DOCUMENTS
3,857,094 A * 12/1974 Caldecourt .................. 324/700
(Continued)

FOREIGN PATENT DOCUMENTS
DE    195 43 060 A1    5/1997
(Continued)

OTHER PUBLICATIONS
Falko Wachholz, Jan Gimsa, Heiko Duewensee, Harald Grabow, Peter Grundler, Gerd-Uwe Flechsig, A Compact and Versitile Instrument for Radio Frequency Heating in Nonisothermal Electrochemical Studies, Electroanalysis, 19, No. 5, 535-540, First Available Online Jan. 29, 2007.*
Lau, et al., "Electrochemistry of Nicotinamide Adenine Dinucleotide (Reduced) at Heated Platinum Electrodes", Analytica Chimica Acta, 2005, p. 74-78, #554, Elsevier.
(Continued)

Primary Examiner — Jeffrey T Barton
Assistant Examiner — Maris R Kessel
(74) Attorney, Agent, or Firm — Laurence A. Greenberg; Werner H. Stemer; Ralph E. Locher (57) ABSTRACT

A sensor apparatus for an electrochemical measuring device. The apparatus has at least one electrode, which can be heated using a heating current in the form of an alternating current, and a first and a second connection for the supply line for the heating current. The electrochemical measuring device is connected to the electrode by a third connection. In this case, the apparatus has the third connection connected to the electrode by a bridge circuit, which is also connected to the first and second connections. There also is provided a method for carrying out electrochemical measurements at elevated temperature. The sensor apparatus and the method for carrying out electrochemical measurements enable electrochemical measurements with little interference and directly heated electrodes in conjunction with a simplified design of the electrodes.

23 Claims, 4 Drawing Sheets

U.S. PATENT DOCUMENTS

| | | | |
|---|---|---|---|
| 5,576,563 | A | 11/1996 | Chung |
| 5,693,545 | A | 12/1997 | Chung et al. |
| 5,786,608 | A | 7/1998 | Lescouzeres et al. |
| 5,879,630 | A | 3/1999 | Lescouzeres et al. |
| 6,255,677 | B1 | 7/2001 | Caillat et al. |
| 6,428,749 | B1 | 8/2002 | Kajiyama et al. |
| 2007/0164211 | A1 | 7/2007 | Flechsig et al. |

FOREIGN PATENT DOCUMENTS

| | | |
|---|---|---|
| DE | 19842735 A1 | 3/2000 |
| DE | 199 60 398 A1 | 6/2001 |
| DE | 10 2004 017 750 A1 | 10/2005 |
| EP | 0 794 427 A1 | 9/1997 |
| EP | 0 795 747 B1 | 9/1997 |
| EP | 1 108 472 B1 | 6/2001 |
| WO | 2005/098438 A1 | 10/2005 |

OTHER PUBLICATIONS

Gabrielli et al., "A Temperature Perturbation Method For Electrochemical Kinetics Investigations", J. Electroanal. Chem., 148 (1983) pp. 293-297.

Zerihun et al., "Electrically heated cylindrical microelectrodes. The reduction of dissolved oxygen on Pt", Journal of Electroanalytical Chemistry and Interfacial Electrochemistry 404 (1996) 243-248, XP005278119.

Flechsig et al., "DNA hybridization detection at heated electrodes" Langmuir 21 (2005), 7848-7853, XP002378872.

Baranski, "Hot Microelectrodes", Analytical Chemistry 74 (2002) 1294-1301, XP001115333.

International Preliminary Report on Patentability and Written Opinion dated Sep. 18, 2008.

* cited by examiner

SENSOR APPARATUS FOR AN ELECTROCHEMICAL MEASURING DEVICE AND METHOD FOR CARRYING OUT ELECTROCHEMICAL MEASUREMENTS

BACKGROUND OF THE INVENTION

Field of the Invention

The invention relates to a sensor apparatus for an electrochemical measuring device having at least one electrode, which can be heated by means of a heating current formed as an alternating current and comprises a first and a second terminal for supplying the heating current, the electrochemical measuring device being connected to said electrode through a third terminal, and to a method for carrying out electrochemical measurements at high temperature by using a sensor apparatus with an electrode heated directly by an electrical heating current formed as an alternating current, the electrochemical measurements taking place simultaneously with the electrical heating of the electrode.

Such a sensor apparatus for an electrochemical measuring device is used for electrochemical measurements so that, by recording electrochemical reactions, for example substances can be detected, their state or their concentration can be determined or thermodynamic and/or kinetic parameters of the electrochemical reactions can be found. The sensor apparatus for an electrochemical measuring device comprises at least one electrode, by means of which an electrochemical signal is recorded.

In order to carry out electrochemical measurements at high temperatures, it is conventional to use electrochemical cells which are brought to the desired temperature by thermostatting with water as a heat transfer medium, the quantity of electrolyte contained in the electrochemical cells being heated. Such arrangements are disadvantageous since large amounts of energy are needed in order to heat the electrochemical cell, temperature changes take place only very slowly and sensitive substances in the electrolyte solution can be affected by the heating.

In order to overcome these disadvantages, sensor apparatus may therefore comprise electrodes which can be heated indirectly or directly by means of a heating current.

In the case of an indirectly heated electrode, the electrode is heated by means of heating elements DC-electrically separated from the electrode, which complicate the structure of the sensors, likewise cause heating of at least a large part of the electrolyte solution and therefore allow only slow temperature changes, and which make it much more difficult to miniaturize the electrodes.

In the case of directly heated electrodes on the other hand, the electrodes are heated by a radiofrequency alternating current constituting a heating current, which is applied to the electrode through two terminals and flows through the electrode, and thereby heats the electrode directly. For connecting the electrochemical measuring device, the electrode comprises a third terminal which is arranged centrally on the electrode, symmetrically with respect to the two terminals in order to permit interference-free electrochemical measurement. This arrangement of the terminal for the electrochemical measuring device substantially avoids interfering effects of the heating current on the electrochemical measurement signals.

A disadvantage of conventional sensor apparatus with directly heated electrodes is however the complicated structure of the electrodes, each having three terminals connected to the electrode, which makes it much more difficult to use electrode arrays with a multiplicity of electrodes and greatly restricts the possibilities of miniaturizing such electrode arrangements. A further disadvantage is that only small tolerances are allowed during the production process in respect of the symmetrical arrangement of the electrode's third terminal, used for connection to the electrochemical measuring device, so that interference signals caused by the heating current and picked up during a measurement can be kept small. The electrode furthermore experiences thermal interference owing to the central terminal, which is connected to the electrochemical measuring device and dissipates heat, so that temperature gradients may be formed over the electrode's reaction surface by means of which the electrochemical signal is recorded.

BRIEF SUMMARY OF THE INVENTION

It is an object of the invention to provide a sensor apparatus for an electrochemical measuring device and a method for carrying out electrical measurements, which permit low-interference electrochemical measurements by directly heated electrodes with a simplified structure of the electrodes.

This object is achieved by an article having the features of claim 1.

According to the invention, a sensor apparatus for an electrochemical measuring device comprises at least one electrode, which can be heated by means of a heating current formed as an alternating current and comprises a first and a second terminal for supplying the heating current. The electrochemical measuring device is connected to the electrode through a third terminal, the connection of the third terminal to the electrode being formed through a bridge circuit which is connected to the first and second terminals.

The sensor apparatus according to the invention provides a sensor which on the one hand permits virtually interference-free measurements and on the other hand has a simplified structure, since the at least one electrode of the sensor apparatus now comprises only two terminals and the terminal for the electrochemical measuring device is connected to the two heating current terminals through a bridge circuit. Decoupling of the heating current from the electrochemical signal, recorded by the measuring device, is achieved by means of the bridge circuit. The bridge circuit acts as a hum suppressor circuit, by means of which the heating current is for the most part conducted through the electrodes and the terminal of the electrochemical measuring device is connected through the bridge circuit to the terminals for the heating current on the electrode so as to precisely compensate for the interfering effects of the heating current. Because the electrode makes do with two terminals, it furthermore avoids temperature gradients and excessive heat loss through additional terminals arranged on the electrode.

The heating current is preferably formed as an alternating current with a frequency of at least 1 kHz, but preferably greater than or equal to 100 kHz.

In contrast to the heating current, the electrochemical signal to be recorded by the sensor apparatus may however be a temporally virtually constant or temporally varying signal, which is generally formed as a low-frequency signal with frequencies much lower than the frequency of the heating current.

The sensor apparatus is preferably designed so that the bridge circuit comprises two symmetrical terminal arms which are connected at one of their ends to one of the two terminals for supplying the heating current and are connected at their other end to one another and to the terminal of the electrochemical measuring device. Through the two symmetrical terminal arms, the electrochemical measuring device is thus connected to the terminals for the heating current and therefore to the electrode, without a separate terminal for the electrochemical measuring device needing to be arranged on the electrode itself and therefore so as to provide an arrangement having an electrode with only two terminals. The effect achieved by the symmetrical design of the terminal arms is that the interfering signals of the heating current are mutually eliminated at the terminal of the electrochemical measuring device.

The two terminal arms of the bridge circuit preferably comprise symmetrically formed, i.e. equivalently acting inductors. These inductors have a blocking effect for the radiofrequency heating current since they have a large impedance for signals with high frequency. For a low-frequency electrochemical signal the impedance of the inductors is negligible, however, so that the electrochemical signals can travel virtually unimpeded through the terminal arms to the electrochemical measuring device. The inductors arranged as a bridge circuit therefore act as a filter which suppresses the interfering heating current signal, but conducts the electrochemical signal to be measured to the terminal of the electrochemical measuring device.

In order to obtain the desired filter behavior and achieve sufficient suppression of the interference signals, the inductors in the terminal arms between the terminal of the electrochemical measuring device and the two terminals for supplying the heating current are advantageously designed so that they have an inductance of more than 1 mH, in particular more than 100 mH, and a resistance of less than 1 ohm.

In a preferred configuration of the sensor apparatus, an additional inductor, through which the electrochemical measuring device is connected to the two terminal arms of the bridge circuit, is arranged in a terminal branch between the terminal of the electrochemical measuring device and the junction of the two terminal arms of the bridge circuit. Additional attenuation of interfering signals and therefore an improvement in the transfer behavior can be achieved by means of the inductor in the terminal branch of the electrochemical measuring device, since the inductor in the terminal branch presents a large impedance for an interfering radiofrequency heating current signal but is negligible for a low-frequency electrochemical signal.

The inductor in the terminal branch also advantageously has an inductance of more than 1 mH, in particular more than 100 mH, and a resistance of less than 1 ohm.

In a preferred configuration, a capacitor, which connects the terminal branch to a reference ground, may respectively be arranged before and after the inductor in the terminal branch. In this way, the inductor in the terminal branch and the capacitors arranged before and after the inductor, between the terminal branch and the reference ground, respectively form a blocking circuit which can be tuned so that for example a signal with the frequency of the heating current is blocked and therefore virtually fully suppressed at the terminal of the electrochemical measuring device. Interfering effects by the heating current on the terminal of the electrochemical measuring device can be virtually fully suppressed in this way. The electrochemical measuring device then records an electrochemical signal with a large signal-to-noise ratio, which permits sensitive measurements without significantly complicating the structure of the arrangement.

Instead of the inductors or in addition to the inductors, in a variant of the sensor apparatus symmetrically arranged resistors may also be arranged in the two terminal arms of the bridge circuit. Such an arrangement may be expedient in particular for recording higher-frequency electrochemical signals, in order to avoid distortion of the electrochemical signal by inductors and at the same time to achieve sufficient suppression of the interfering heating current signals.

The resistors in the terminal arms then preferably have a resistance which is at least an order of magnitude greater than the resistance of the electrode. The effect achieved in this way is that the heating current essentially flows through the electrode and only to a small part through the bridge circuit. The decoupling of the heating current signal flowing through the bridge circuit from the electrochemical signal to be recorded is then carried out essentially by the symmetrical design of the two terminal arms of the bridge circuit, owing to which the heating current signals flowing through the bridge circuit are precisely compensated for at the terminal point of the electrochemical measuring device.

In an advantageous configuration of the sensor apparatus, a resistor is additionally arranged in the terminal branch between the terminal of the electrochemical measuring device and the two terminal arms of the bridge circuit, by means of which a further improvement can be achieved in the transfer behavior, in particular the effective signal-to-noise ratio at the terminal of the electrochemical measuring device.

In an advantageous variant of the sensor apparatus, a variable resistor is provided between the terminal branch and the two terminal arms of the bridge circuit, by means of which precise balancing of tolerances in the terminal arms and the bridge circuit's components arranged in the terminal arms can be carried out.

In another variant, inductors and/or resistors are arranged in any desired combination in the two terminal arms and in the terminal branch, the terminal branch being connected to the two terminal arms of the bridge circuit through a variable resistor acting as a voltage divider.

The object is furthermore achieved by a method having the features of claim 15.

According to the invention, a method for carrying out electrochemical measurements at high temperature by using the sensor apparatus according to the invention employs an electrode heated directly by an electrical heating current formed as an alternating current. The electrochemical measurements take place simultaneously with the electrical heating of the electrode, a bridge circuit being used to connect an electrochemical measuring device to the electrode and the bridge circuit suppressing interference signals generated by the heating current at the terminal of the electrochemical measuring device.

It therefore provides a method, by means of which electrochemical measurements can be carried out at high temperatures by using a directly heated electrode. The method allows the interference signals caused by the heating current to be suppressed, so that they do not interfere with the acquired electrochemical signal.

It is conceivable and advantageous, for example, for electrochemical measurements to be carried out by using voltammetry, amperometry, potentiometry, chronopotentiometry, stripping potentiometry, coulometry and/or chronocoulometry in order to determine substance concentrations.

The electrochemical measurements may furthermore be carried out by using cyclovoltammetry, impedance spectroscopy and/or spectroelectrochemistry in order to study electrode processes, in particular the thermodynamics and kinetics of electrode reactions, deposition of layers and corrosion.

In an advantageous variant of the method, the electrical heating of the electrode is carried out by means of short heating current pulses, preferably shorter than 500 ms, in particular shorter than 100 ms. The electrochemical measurement of the electrochemical signal may take place before the start and/or shortly before the end of each heating current pulse.

In another configuration, a temporally constant potential is applied to the heated electrode in order to carry out amperometry, or a temporally linearly varying potential in order to carry out voltammetry.

The underlying concept of the invention will be explained in more detail below with the aid of the figures represented in the drawings, in which:

DESCRIPTION OF THE INVENTION

1. Structure of the Sensor Apparatus

FIGS. 1-4 show various embodiments of a sensor apparatus for an electrochemical measuring device having an electrode 1, which can be heated directly by a heating current. The electrode 1 comprises terminals 13 to which a supply voltage 3 is applied via a transformer 2 and generates a heating current through the electrode 1 by means of the transformer 2. A terminal 5 for an electrochemical measuring device is connected to the terminals 13 of the electrode 1 through a bridge circuit 10. The electrode 1 therefore comprises only two terminals 13 through which on the one hand a heating current, by which the electrode 1 is heated, is applied to the electrode and on the other hand the terminal 5 for the electrochemical measuring device is connected to the electrode 1.

The terminal 5 connected through the bridge circuit 10 to the terminals 13, and therefore to the electrode 1, is used for connection to the electrochemical measuring device. The electrochemical measuring device records electrochemical signals, which are measured by means of the electrode 1 and conducted through the bridge circuit 10 to the terminal 5. The bridge circuit 10 respectively comprises two terminal arms 11, which are formed symmetrically and are connected at one of their ends to the terminal 13 of the electrode 1 and at their other end to one another and to the terminal 5. The effect achieved by the symmetrical design of the terminal arms 11 of the bridge circuit 10 is that interfering effects, which are generated by the heating current that flows through the electrode 1, are mutually compensated for precisely at the terminal 5 of the electrochemical measuring device. This is due to the fact that, owing to the symmetrical design of the terminal arms 11, the ends of the terminal arms 11 of the bridge circuit 10 which are connected to the terminal 5 precisely constitute a point of virtual ground for the heating current at their junction because the two terminals 13 of the heating current are at opposing potentials owing to the applied supply voltage 3, so that the heating current signal is negligible at the junction of the terminal arms 11 and therefore at the terminal 5 for the electrochemical measuring device. the effect achieved by this is that interference due to the heating current flowing through the electrode 1 is substantially suppressed at the terminal 5 of the electrochemical measuring device.

On the other hand, the electrochemical signal, which is measured by the electrode 1 and conducted through the bridge circuit 10 to the terminal 5, is not suppressed but is constructively superposed at the junction of the two terminal arms 11 and is conducted through a terminal branch 12 to the terminal 5.

FIGS. 1-4 represents circuit diagrams with various embodiments of the bridge circuit 10. The embodiments according to FIGS. 1-4 differ on the one hand in the components 4, 6 used for the terminal branches 11 of the bridge circuit 10 and, on the other hand, by the components 7, 8, 9 arranged in the terminal branch 12 which connects the terminal 5 for the electrochemical measuring device to the terminal arms 11 of the bridge circuit 10.

Figure 1:
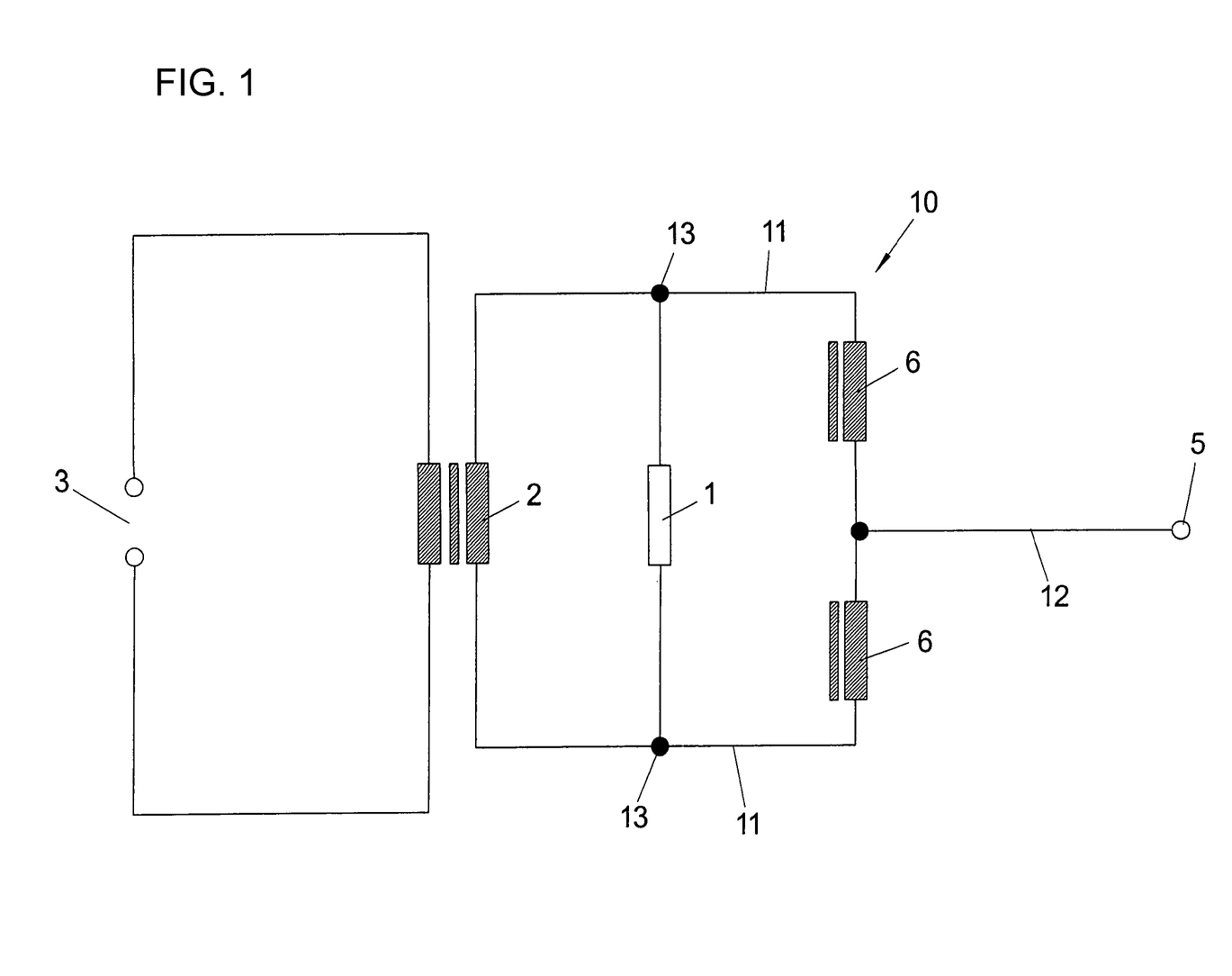
FIG. 1 shows a circuit diagram of a sensor apparatus for an electrochemical measuring device having an electrode and a bridge circuit comprising inductors.

In the sensor apparatus of FIG. 1 an inductor 6 is arranged in each of the terminal branches 11 of the bridge circuit 10, the inductors 6 respectively being connected at one of their ends to the terminal 13 of the electrode 1 and at their other end through the terminal branch 12 to the terminal 5 for the electrochemical measuring device. With this design of the sensor apparatus, the suppression of the interfering heating current signal at the terminal 5 is carried out by twofold measures. On the one hand, interfering heating current signals are mutually compensated substantially at the terminal 5 owing to the symmetrical configuration of the terminal arms 11 of the bridge circuit 10. On the other hand, the inductors 6 act as high-value impedances for the radiofrequency heating current signal having a frequency of at least 1 kHz, but preferably more than 100 kHz. The inductors 6 therefore suppress the radiofrequency heating current signal and prevent transfer of the interfering heating current signal to the terminal 5. For the low-frequency electrochemical signal which is measured by the electrode 1, on the other hand, the impedances of the inductors 6 are negligibly small so that the measured electrochemical signal is conducted virtually unimpeded to the terminal 5. The bridge circuit 10 therefore acts as a filter which on the one hand suppresses the interfering heating current signal, but on the other hand transmits the measured electrochemical signal unimpeded so that an electrochemical signal with a large signal-to-noise ratio can be recorded sensitively at the terminal 5.

Figure 2:
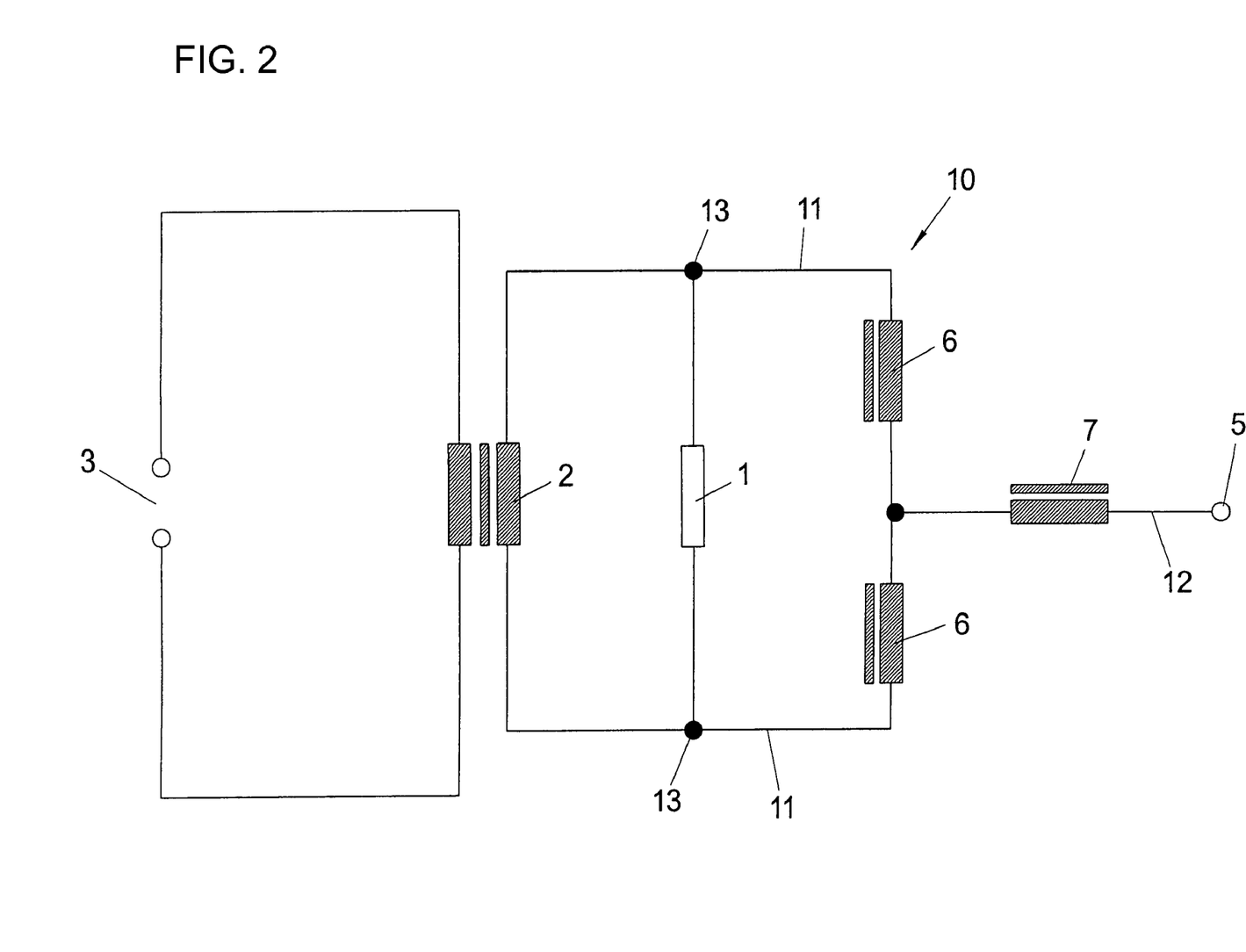
FIG. 2 shows a circuit diagram of the sensor apparatus according to FIG. 1 with an additional inductor in the terminal branch of an electrochemical measuring device.

A refinement of the sensor apparatus according to FIG. 1 is represented in FIG. 2. In the sensor apparatus according to FIG. 2 an inductor 7 is provided in the terminal branch 12, which connects the terminal 5 to the bridge circuit 10, in addition to the bridge circuit 10 comprising inductors 6. Similarly as the inductors 6, the inductor 7 in the terminal branch 12 acts as a high impedance for the radiofrequency heating current signal but as a low impedance for the electrochemical signal to be recorded. The interfering heating current signals are therefore additionally suppressed by the inductor 7, and an additional improvement can be achieved in the transfer behavior of the sensor apparatus.

Figure 3:
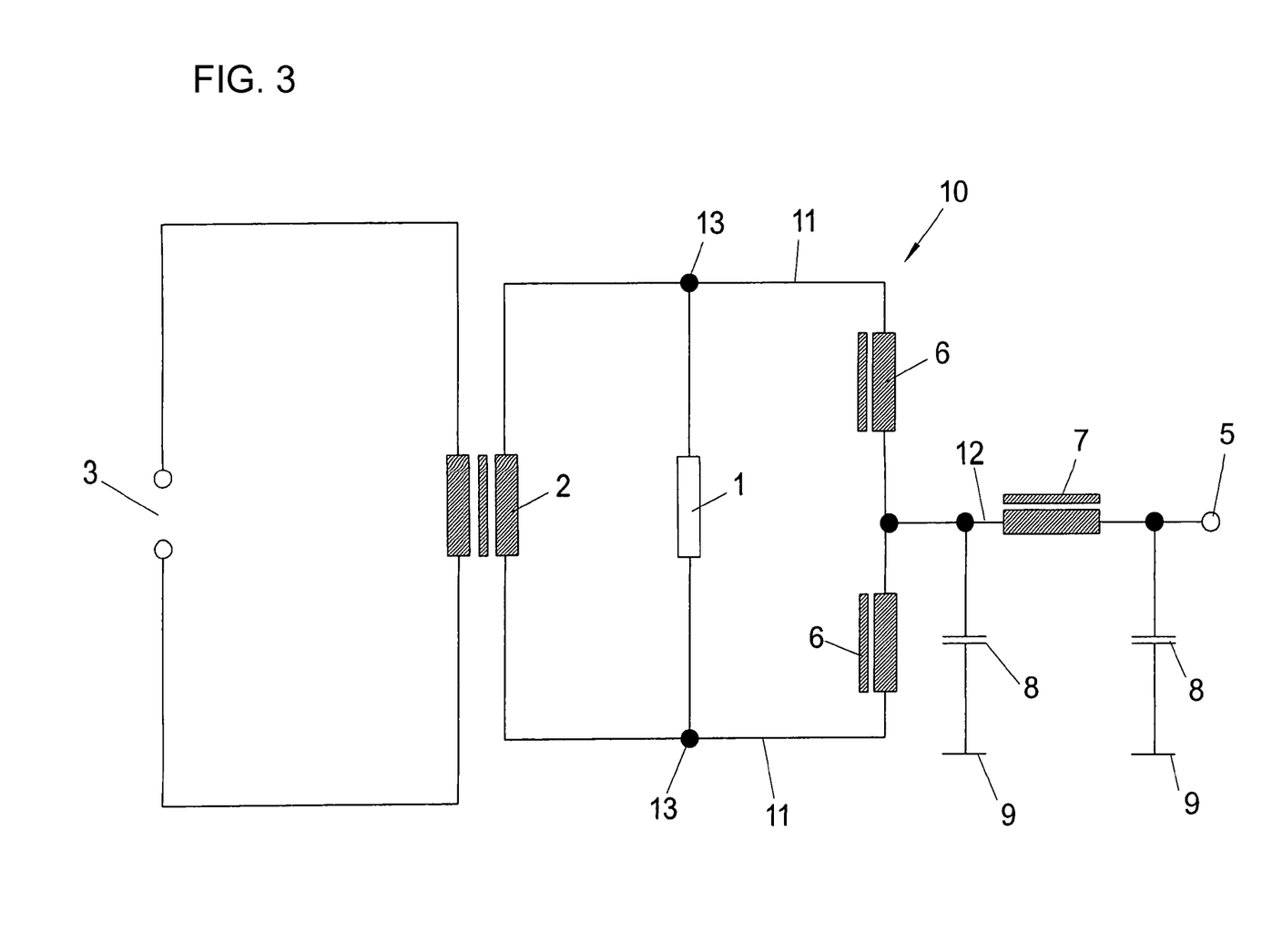
FIG. 3 shows a circuit diagram of the sensor apparatus according to FIG. 2 with capacitors arranged before and after the inductor in the terminal branch of the electrochemical measuring device.

In order to improve the transfer behavior of the sensor apparatus further, it is possible to use capacitors which form a blocking circuit with the inductor 7 in the terminal branch 12. Such a design of the sensor apparatus is represented in FIG. 3. Before and after the inductor 7 in the terminal branch 12 of the arrangement in this arrangement, a capacitor 8 is respectively provided which acts as a so-called shunt between the terminal branch 12 and the reference ground 9. Together with the inductor 7, for certain frequencies the capacitors 8 have a blocking circuit behavior which can be adjusted through the capacitances and inductances of the capacitors 8 and the inductor 7, respectively. The blocking frequency of the blocking circuit formed by the capacitors 8 and the inductor 7 is preferably tuned to the frequency of the heating current, so that an interfering heating current signal residually present in the terminal branch 12 can be suppressed virtually fully by the blocking circuit. Another effect achievable by this is that a relatively weak electrochemical signal can be measured at the terminal 5.

The designs of the electrochemical sensor apparatus as represented in FIGS. 1-3 are expedient in particular when using radiofrequency heating current signals and recording low-frequency, in particular temporally virtually invariant electrochemical signals. If temporally varying electrochemical signals are intended to be recorded, however, then the inductors 6, 7 of the arrangements according to FIGS. 1-3 cause an undesired interfering distortion of the electrochemical signal to be measured. In order to avoid this, instead of the inductors 6 in the terminal arms 11 of the bridge circuit 10, it is possible to use resistors 4 whose resistance is at least an order of magnitude, but preferably two orders of magnitude greater than the resistance presented by the electrode 1 to the heating current. This will mean that the heating current flows essentially from the terminals 13 though the electrode 1 and only a fraction of it is conducted through the terminal arms 11 of the bridge circuit 10. The compensation for the interfering heating current signals is then carried out essentially by the symmetrical design of the terminal arms 11 with the resistors 4 of the bridge circuit 10.

Figure 4:
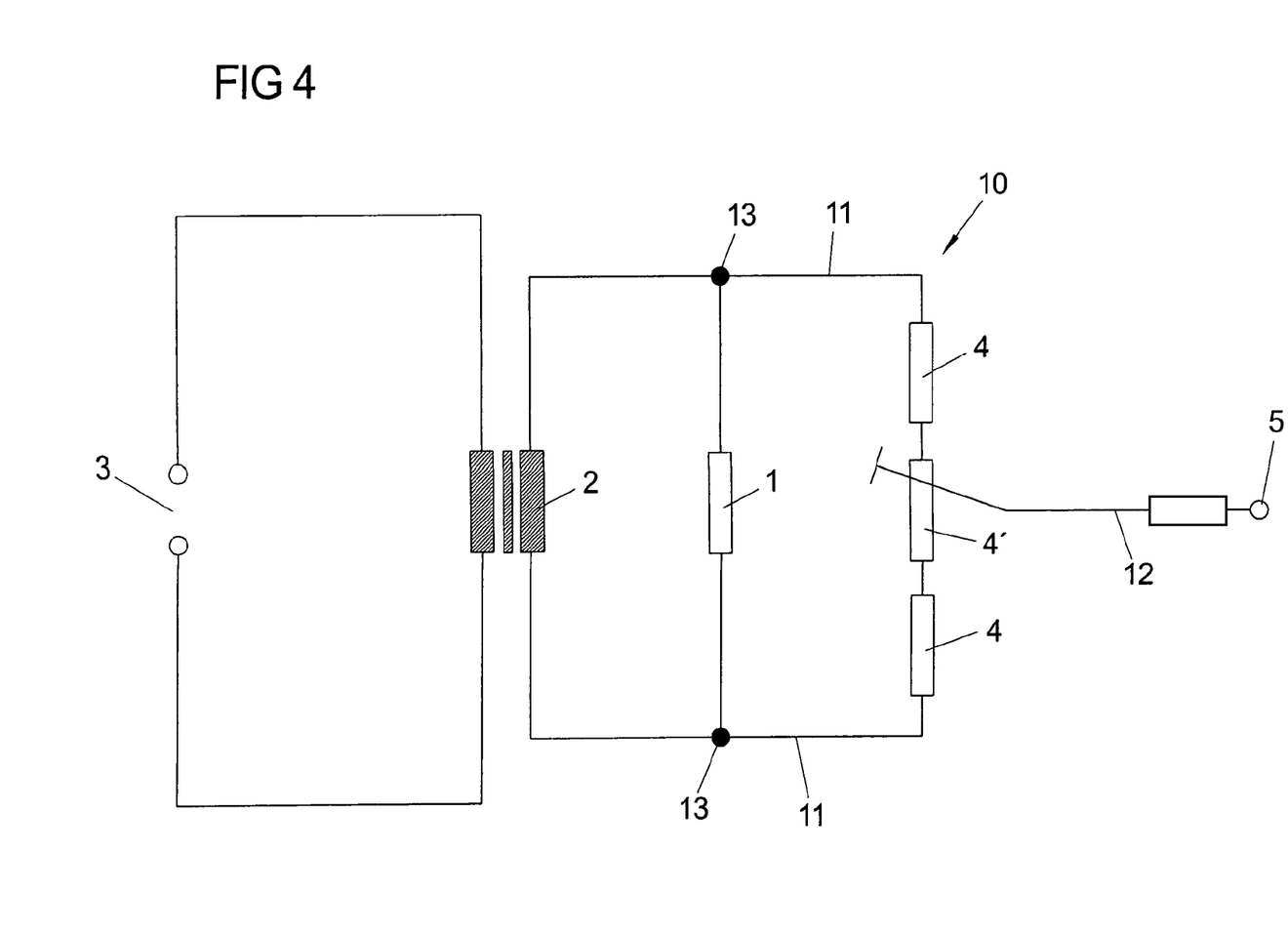
FIG. 4 shows a circuit diagram of a sensor apparatus having an electrode and a bridge circuit comprising resistors.

In the sensor apparatus according to FIG. 4, it may then be advantageous to connect the terminal 5 for the electrochemical measuring device to the terminal arms 11 of the bridge circuit 10 through a terminal branch 12 and an additional variable resistor 4'. By means of the variable resistor 4', it is then possible to adapt the compensation of the interfering heating current signals so as to be able to balance tolerances and compensate for asymmetries in the terminal arms 11 of the bridge circuit 10.

2. Electrochemical Measurements by Means of the Sensor Apparatus

The sensor apparatus, the basic concept of which has been explained above with the aid of FIGS. 1 to 4, may be used in a multiplicity of applications which are described by way of example below.

EXAMPLE 1

For selective electrochemical recording of the PCR products formed in the course of a polymerase chain reaction (PCR), an electrode 1 designed as a directly heatable gold wire electrode is used, which has DNA probe strands immobilized by thiol linkers on its surface. The effect achieved by setting a stringent electrode temperature during the hybridization is that only PCR products with the sequence complementary to the probe strands can be bound on the electrode surface. The stringent temperature has a value 5 K lower than the melting temperature associated with the sequence to be detected. At their melting temperature, nucleic acid double strands are separated into single strands. The electrochemical detection is carried out with the aid of a reporter strand, which likewise has a sequence complementary to the PCR product to be detected and can be marked with the reversibly electrochemically active marker ferrocene. The effect achieved by the bridge circuit 10, which according to the invention is connected to the electrode 1 and by means of which an electrochemical measuring device is coupled to the electrode 1, is that, while the heating current is flowing, the nine orders of magnitude weaker electrochemical signals of the ferrocene-marked reporter strands can be registered without having to use a symmetrical electrode arrangement that provides a third terminal for the electrochemical measuring device directly on the electrode. Omission of the third terminal directly on the electrode facilitates the precise adjustment of a uniform electrode temperature, which is a prerequisite for stringent recording of the desired PCR products at the complementary probe strands immobilized on the electrode.

EXAMPLE 2

In order to determine the kinetics of the enzyme glucose oxidase simultaneously at temperatures of 0° C., 10° C., 20° C., 30° C., 40° C., 50° C. and 60° C., an electrode array consisting of a multiplicity of directly heatable electrodes 1 is used. The reaction surfaces, i.e. the surfaces of the electrodes 1 on which the electrochemical signal is recorded, are modified with glucose oxidase by inclusion in a coating layer and put into an electrochemical cell. The electrolyte in the cell contains 20 mM glucose and 0.05 M phosphate buffer with a pH of 7, and is kept at 0° C. by thermostatting. By selective heating, the individual reaction surfaces of the electrodes 1 are brought to said temperatures between 0° C. and 60° C. The kinetics of the enzyme are determined amperometrically by the hydrogen peroxide which is formed being oxidized on the individual electrodes 1 of the electrode array. Owing to the inventive connection of an electrochemical measuring device to the individual electrodes 1 of the electrode array in each case by means of the bridge circuit 10, only two terminals are required per electrode 1 and at the same time the interference signal, which is caused by the heating current and is about six orders of magnitude stronger than the electrochemical signal, is minimized. The structure of the electrode array and the driving of the multiplicity of electrodes 1 are greatly simplified by using two terminals per electrode 1 in each case, compared with electrode arrangements which employ three symmetrical terminals.

EXAMPLE 3

In a flow system, compounds which enter into kinetically hindered reactions at an electrode can be determined by means of amperometry. For example aromatic nitro compounds such as TNT and dinitrobenzene can be determined in the ultra-trace range (ppb to ppm). To this end a heatable platinum wire electrode 1, which is connected through the bridge circuit 10 to the electrochemical measuring device, is used as an electrode 1. During the amperometric measurements, the electrode 1 is heated so that the kinetically hindered reduction of the nitro groups takes place in an accelerated fashion. Owing to the inventive connection of the electrochemical measuring device through the bridge circuit 10, only two terminals 13 are required on the heated platinum wire electrode 1. Since only one platinum wire electrode is required as an electrode 1 for the sensor apparatus in the flow system for this application, a simply constructed directly heatable sensor apparatus is obtained.

EXAMPLE 4

The determination of aromatic nitro compounds according to Example 3 can be carried out at temperatures above the boiling point of the electrolyte by employing so-called temperature pulse amperometry. This is made possible by the use of very short (preferably shorter than 100 ms) heating pulses which heat an aqueous electrolyte to temperatures of more than 200° C. Kinetically hindered reactions can be accelerated considerably in this way. With a constant negative potential applied to the electrode 1 in order to reduce the nitro groups, a measurement is respectively taken before the start and before the end of the heating pulses, the difference between them being formed. With small amounts of electrolyte (10 ml) and using the sensor in narrow flow systems (diameter less than 1 mm), shorter heating pulses (1 to 50 ms) are used in order to reduce the amount of heat generated. The heating current strength should be increased in this case in order to achieve the same temperature in a shorter time. Owing to the bridge circuit 10 according to the invention for connecting the electrochemical measuring device, only two terminals 13 are required on the heated platinum wire electrode 1.

EXAMPLE 5

The determination of aromatic nitro compounds can be carried out similarly as in Example 3 but by employing temperature pulse voltammetry according to a method known from DE 195 43 060 A1. A linear voltage ramp is implemented in a negative direction and short heating current pulses are applied in superposition with this. The electrochemical measurement is carried out before the start and before the end of each heating current pulse. The difference between the two measurements is used as an electrochemical analysis signal. In this application as well, only two terminals 13 are required on the heated platinum wire electrode 1 owing to inventive connection of the electrochemical measuring device, which leads to a simplification in the structure of the sensor apparatus.

EXAMPLE 6

Heated platinum electrodes may be used vary advantageously for the determination of nicotinamide adenine dinucleotide (NADH) (cf. C. Lau, G.-U. Flechsig, P. Gründler, J. Wang, Anal. Chim. Acta 554 (2005), pages 74-78). Accordingly, a considerable increase in the amperometric NADH signal can be achieved when the determination is carried out at elevated electrode temperatures but the analysis solution is kept at a constant temperature. The so-called "sensor fouling", which causes the recorded electrochemical signals to decrease with each measurement, can be reduced in this way. In this case as well, the inventive connection of a directly heated platinum electrode permits a very simple structure of a sensor apparatus for the detection of NADH, in which case the platinum electrodes may for example contain platinum wires layers and negligible interference signals are conducted to the electrochemical measuring device.

LIST OF REFERENCES

1 electrode
2 transformer
3 supply voltage
4 resistor in the terminal arm of the bridge circuit
4' variable resistor
5 terminal of the electrochemical measuring device
6 inductor in the terminal arm of the bridge circuit
7 inductor in the terminal branch of the electrochemical measuring device
8 capacitor
9 ground
10 bridge circuit
11 terminal arm of the bridge circuit
12 terminal branch of the electrochemical measuring device
13 terminal for the heating current

The invention claimed is:

1. A sensor apparatus for an electrochemical measuring device comprising:
   at least one electrode for being heated by an alternating heating current;
   first and second terminals for supplying the heating current;
   a transformer operative to supply a voltage to said first and second terminals for supplying the heating current to said at least one electrode;
   a third terminal for connecting the electrochemical measuring device to said at least one electrode; and
   a bridge circuit connected to said first and second terminals and connecting said third terminal to said at least one electrode;
   wherein said bridge circuit includes two symmetrical terminal arms having one end connected to one of said first and second terminals for supplying the heating current and another end connected to each other and to said third terminal.

2. The sensor apparatus according to claim 1, wherein the alternating heating current has a frequency of at least 1 kHz.

3. The sensor apparatus according to claim 2, wherein the alternating heating current has a frequency greater than or equal to 100 kHz.

4. The sensor apparatus according to claim 1, wherein said sensor apparatus has a recordable electrochemical signal.

5. The sensor apparatus according to claim 1, wherein said two terminal arms of said bridge circuit comprise symmetrically configured inductors.

6. The sensor apparatus according to claim 1, wherein said two terminal arms of said bridge circuit comprise symmetrically configured ohmic resistors.

7. A sensor apparatus for an electrochemical measuring device comprising:
   at least one electrode for being heated by an alternating heating current;
   first and second terminals for supplying the heating current;
   a third terminal for connecting the electrochemical measuring device to said at least one electrode; and
   a bridge circuit connected to said first and second terminals and connecting said third terminal to said at least one electrode, said bridge circuit having two symmetrical terminal arms which are connected at one of their ends to one of said first and second terminals for supplying the heating alternating current and are connected at their other end to each other and to said third terminal, said two terminal arms of said bridge circuit include symmetrically configured inductors, said inductors each having an inductance of more than 1 mH and a resistance of less than 1 ohm.

8. The sensor apparatus according to claim 7, wherein said inductors each have an inductance of more than 100 mH.

9. A sensor apparatus for an electrochemical measuring device comprising:
   at least one electrode for being heated by an alternating heating current;
   first and second terminals for supplying the heating current;
   a third terminal for connecting the electrochemical measuring device to said at least one electrode; and
   a bridge circuit connected to said first and second terminals and connecting said third terminal to said at least one electrode, said bridge circuit having two symmetrical terminal arms which are connected at one of their ends to one of said first and second terminals for supplying the alternating heating current and are connected at their other end to each other and to said third terminal; and an additional inductor arranged in a terminal branch between said third terminal of the electrochemical measuring device and said two terminal arms of said bridge circuit.

10. The sensor apparatus according to claim 9, wherein said additional inductor in the terminal branch has an inductance of more than 1 mH and a resistance of less than 1 ohm.

11. The sensor apparatus according to claim 10, wherein said additional inductor in the terminal branch has an inductance of more than 100 mH.

12. The sensor apparatus according to claim 9, further including a plurality of capacitors connecting said terminal branch to reference ground and respectively arranged before and after said additional inductor in said terminal branch.

13. The sensor apparatus according to claim 6, wherein said ohmic resistors have a resistance at least one order of magnitude greater than a resistance of said at least one electrode.

14. The sensor apparatus according to claim 9, further including a resistor arranged in said terminal branch between said third terminal and said two terminal arms of said bridge circuit.

15. The sensor apparatus according to claim 9, further including a variable ohmic resistor operating as a voltage divider connecting said terminal branch to said two terminal arms of said bridge circuit.

16. The sensor apparatus according to claim 9, further including at least one of an inductor and resistors arranged in said two terminal arms and in said terminal branch, and a variable ohmic resistor operating as a voltage divider connecting said terminal branch to said two terminal arms of said bridge circuit.

17. A method for carrying out electrochemical measurements at high temperature, comprising the steps of:
providing a sensor apparatus according to claim 1;
directly heating an electrode by an electrical alternating heating current;
simultaneously taking electrochemical measurements with the electrical heating of the electrode; and
using the bridge circuit for connecting an electrochemical measuring device to the at least one electrode, the bridge circuit suppressing interference signals generated by the heating current at the terminal of the electrochemical measuring device.

18. The method according to claim 17, including the step of:
carrying out the electrochemical measurements to determine substance concentrations by using any one or more selected from a group consisting of voltammetry, amperometry, potentiometry, chronopotentiometry, stripping potentiometry, coulometry, and chronocoulometry.

19. The method according to claim 17, including the step of:
carrying out the electrochemical measurements to study electrode processes, including thermodynamics and kinetics of electrode reactions, deposition of layers and corrosion, by using any one or more selected from a group consisting of cyclovoltammetry, impedance spectroscopy, and spectroelectrochemistry.

20. The method according to claim 17, including the step of:
electrically heating the electrode using short heating current pulses, preferably shorter than 500 ms; and
electrochemically measuring the electrochemical signal before the start and/or shortly before the end of each heating current pulse.

21. The method according to claim 20, including the step of:
electrically heating the electrode using short heating current pulses, most preferably shorter than 100 ms.

22. The method according to claim 20, including the step of:
electrically heating the electrode by applying a temporally constant potential to the heated electrode to carry out amperometry.

23. The method according to claim 20, including the step of:
applying a temporally linearly varying potential to the heated electrode in order to carry out voltammetry.

* * * * *